(12) United States Patent
Petersen et al.

(10) Patent No.: US 7,169,608 B2
(45) Date of Patent: Jan. 30, 2007

(54) BONE MARROW CELL DIFFERENTIATION

(75) Inventors: Bryon E. Petersen, Gainesville, FL (US); Seh-hoon Oh, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 196 days.

(21) Appl. No.: 10/687,674

(22) Filed: Oct. 17, 2003

(65) Prior Publication Data

US 2004/0157325 A1    Aug. 12, 2004

Related U.S. Application Data

(60) Provisional application No. 60/479,066, filed on Jun. 17, 2003, provisional application No. 60/419,434, filed on Oct. 18, 2002.

(51) Int. Cl.
    *C12N 5/06* (2006.01)
    *C12N 5/08* (2006.01)

(52) U.S. Cl. .................. 435/377; 435/372; 435/375

(58) Field of Classification Search ............... 435/377, 435/372, 375
See application file for complete search history.

(56) References Cited

U.S. PATENT DOCUMENTS

| 6,458,589 B1 | 10/2002 | Rambhatla et al. |
| 2002/0182728 A1* | 12/2002 | Ramiya et al. ............ 435/366 |
| 2003/0104997 A1* | 6/2003 | Black et al. .................. 514/12 |

FOREIGN PATENT DOCUMENTS

| WO | WO/50048 | 8/2000 |
| WO | WO 02/079457 A1 | 10/2002 |
| WO | WO 02/096203 A1 | 12/2002 |
| WO | WO 03/020908 A2 | 3/2003 |
| WO | WO 2004/016747 A2 | 2/2004 |

OTHER PUBLICATIONS

Petersen et al. Bone Marrow as a Potential Source of Hepatic Oval Cells. Science. May 1999, vol. 284, pp. 1168-1170.
Yang et al. In Vitro Transdifferentiation of Adult Hepatic Stem Cells into Pancreatic Endocrine Hormone Producing Cells. PNAS, Jun. 2002, vol. 99, No. 12, pp. 8078-8083.
Yang et al. In Vitro Transdifferentiation of Adult Hepatic Stem Cells into Pancreatic Endocrine Cells. Blood. Nov. 2001, vol. 98, No. 11, part 1, p. 548a.
Ricordi et al. Indefinite Survival of Rat Islet Allografts Following Infusion of Donor Bone Marrow Without Cytoablation. Cell Transplantation. 1996, vol. 5, No. 1, pp. 53-55.
Ende et al., Effect of human umbilical cord blood cells on glycemia and insulitis in type 1 diabetic mice, Biochemical & Biophysical Research Communications, 325:665-669 (2004).
Soria et al., From stem cells to beta cells: new strategies in cell therapy of diabetes mellitus, Diabetologia, 44:407-415 (2001).
Oh et al., Adult bone marrow-derived cells transdifferentiating into insulin-producing cells for the treatment of type 1 diabetes, Laboratory Investigation, 84:607-617 (2004).

* cited by examiner

*Primary Examiner*—Vera Afremova
(74) *Attorney, Agent, or Firm*—Akerman Senterfitt; Nicholas A. Zachariades

(57) ABSTRACT

Bone marrow cells are induced to differentiate into pancreatic hormone-producing cells in vitro and to repopulate a pancreas in vivo. These insulin-producing cells can be used to regenerate a damaged pancreas and reverse hyperglycemia in mammals.

8 Claims, 2 Drawing Sheets

BONE MARROW CELL DIFFERENTIATION

CROSS REFERENCE TO RELATED APPLICATION

This application claims the priority of U.S. provisional patent application No. 60/419,434, filed Oct. 18, 2002 and U.S. provisional patent application No. 60/479,066, filed Jun. 17, 2003.

STATEMENT AS TO FEDERALLY SPONSORED RESEARCH

This invention was made with United States government support under grant numbers DK60015 and DK58614 awarded by the National Institutes of Health. The United States government may have certain rights in the invention.

FIELD OF THE INVENTION

The invention relates generally to the fields of developmental biology and medicine. More particularly, the invention relates to in vitro and in vivo methods for producing endocrine hormone-producing cells from bone marrow (BM) cells and for repairing a damaged pancreas.

BACKGROUND

Diabetes is one of the leading causes of morbidity and mortality in the United States. The cost for treating this disease in the United States is estimated to be about 98 billion dollars annually. The two most common forms of diabetes are referred to as type I and type II diabetes. Type I and type II diabetes are distinguished in that subjects with the type II form have normal or near normal levels of insulin, while subjects with type I have little or no insulin. Type I diabetes is therefore often referred to as insulin dependent diabetes.

Type I diabetes is characterized by an autoimmune reaction which destroys insulin-producing pancreatic beta (i.e., islet) cells. The proliferative capacity of adult pancreatic islet cells is limited. Pancreatic islet cell replacement represents one approach in the treatment of type I and insulin-requiring type II diabetes. This prospect of treatment, however, is restricted by the limited availability of donor cells. In addition to the lack of available donor tissue, immune-system mediated rejection of the transplanted tissue is another major impediment to widespread implementation of transplant therapy. The induction of islet cell neogenesis in the adult pancreas would be an important modality for the treatment of diabetes.

SUMMARY

The invention relates to the development of a method for inducing BM cells to differentiate into endocrine hormone-producing cells in vitro and to methods for repairing a damaged pancreas using BM cells. These developments should facilitate the regeneration of a damaged pancreas as well as the practical implementation of transplantation as a method of treating type I diabetes because (1) BM cells transdifferentiated into endocrine hormone-producing cells can provide a source of insulin-producing cells, and (2) the use of such cells for autologous transplantation avoids an immune system-mediated reaction that can lead to rejection of transplanted cells.

Accordingly, the invention features a method of differentiating a mammalian (e.g., rodent or rat) bone marrow cell into an endocrine hormone-producing cell. The method includes the steps of first culturing the bone marrow cell in a low-glucose (e.g., 5.5 mM) medium containing DMSO and then culturing the bone marrow cell in a high-glucose (e.g., 25 mM) medium containing serum under appropriate conditions and for a sufficient amount of time to promote differentiation of the cell into an endocrine hormone-producing cell. The endocrine hormone produced by the cell can be a pancreatic endocrine hormone such as insulin, glucagon, somatostatin, or pancreatic polypeptide. A cell made according to the foregoing method is also within the invention.

In another aspect, the invention features a method for regenerating/repairing a damaged or diseased pancreas. This method includes the step of administering to a subject (e.g., a mammal such as a rat) with a damaged or diseased pancreas at least one BM cell. The damaged pancreas can be a diabetic pancreas that lacks a normal number of beta islet cells and the subject can be one with hyperglycemia caused by diabetes. Administering the at least one BM cell reduces the hyperglycemia in the subject by increasing insulin levels in the subject.

Another aspect of the invention is a method for reversing hyperglycemia in a mammal having diabetes by administering to the mammal a dose of endocrine hormone-producing cells sufficient to reduce the hyperglycemia in the mammal, the hormone-producing cells being made according to a method comprising the steps of: first culturing BM cells in a low-glucose medium containing DMSO; and then culturing the BM cells in a high-glucose medium containing serum under appropriate conditions and for a sufficient amount of time to promote differentiation of the cells into endocrine hormone-producing cells.

Unless otherwise defined, all technical terms used herein have the same meaning as commonly understood by one of ordinary skill in the art to which this invention belongs.

The term "subject," as used herein, means a human or non-human animal, including but not limited to a mammal such as a dog, cat, horse, cow, pig, sheep, goat, chicken, primate, rat, and mouse.

As used herein, the term "differentiation" refers to the conversion of one cell type to another. Differentiation can include, for example, the conversion of a BM cell to a cell having a pancreatic endocrine cell-like phenotype.

By the terms "bone marrow cell" and "BM" is meant any cell found in the bone marrow of an animal at any stage of development from embryo to adult. This may include bone marrow stem cells that reside in the bone marrow at any stage of development of the animal.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
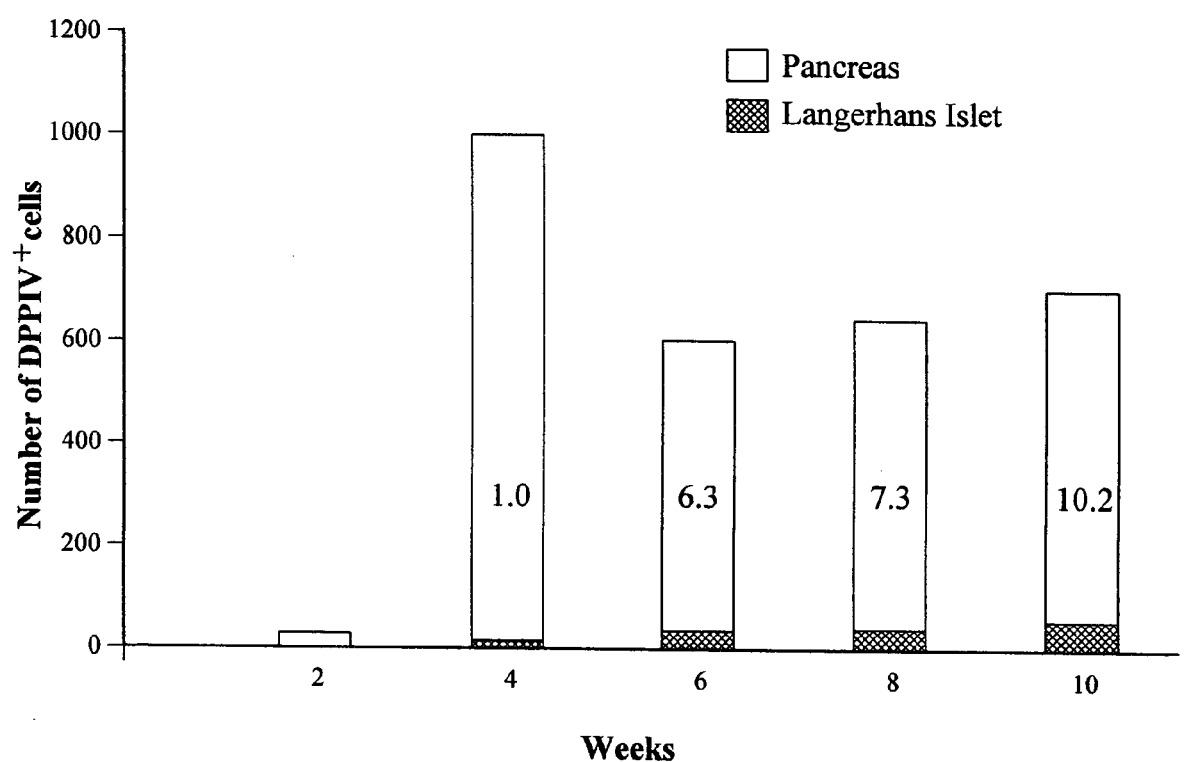
FIG. 1 is a graph showing expression of DPPIV cells in pancreas. DPPIV-expressing cells were counted at 2, 4, 6, 8, and 10 weeks in pancreatic tissues. White bar represents total DPPIV expressing cells and black bar represents DPPIV expressing cells in Langerhans Islet. Numbers are shown as percentages of Langerhans islet cells/total cells that were DPPIV positive.

The invention relates to methods of inducing the differentiation of BM cells into pancreatic cells in vitro, repopulating a pancreas in vivo, and reducing hyperglycemia in vivo. In the invention, a BM cell is differentiated into an endocrine hormone-producing cell (e.g., insulin-producing cell) by first culturing the BM cell first in a low glucose-containing medium containing DMSO, and then culturing the cell in a high glucose-containing medium. This method results in the differentiation of a BM cell into a cell capable of producing pancreatic hormones including insulin, glucagon, somatostatin and pancreatic polypeptide. Pancreatic endocrine hormone-producing cells made in this manner can be used as a renewable source of cells for regenerating a damaged pancreas. The invention therefore also provides a method for producing autologous insulin-producing islet-like cells that can be used to regenerate a damaged pancreas (e.g., for treating patients with type I diabetes).

The below described preferred embodiments illustrate adaptations of these cells and methods. Nonetheless, from the description of these embodiments, other aspects of the invention can be made and/or practiced.

In Vitro Isolation, Culturing and
Trans-Differentiation of BM Cells

The invention is based on the discovery that BM cells can be caused to differentiate into endocrine hormone-producing cells by a two-step culturing process. In the first step, an isolated BM cell is cultured in a serum-free, low-glucose medium containing dimethyl sulfoxide (DMSO). In the second step, the cultured BM cell is further cultured in a high-glucose medium containing serum.

BM cells used in the invention can be isolated according to conventional techniques. For instance, as described in the Examples section below, BM cells are obtained from bone (e.g., femurs and tibias) that has been removed from sacrificed rodents and disinfected. Once the bones are removed and cleaned of skin and muscle, BM cells are exposed by cutting the ends of bones. The cells are then expelled by inserting a needle and forcing a suitable medium (e.g., Iscove's medium supplemented with antibiotic solution) through the bone shaft. BM cells are then passed through a filter (e.g., nylon mesh) to remove any bone pieces that may contaminate the cell suspension. The isolated cells are cultured in a suitable medium (e.g., low-glucose medium containing 10% fetal bovine serum (FBS)) to remove adherent cells, resulting in a population of isolated, non-adherent BM cells.

The first step in the method involves culturing the isolated BM cells in a serum-free, low-glucose medium containing DMSO. This step primes the cells for further differentiation into endocrine hormone-producing (e.g., insulin-secreting) cells. Typically, cells are cultured in this low-glucose medium for approximately 3 days (e.g., 1 to 5 days). In the experiments described below, Dulbecco's Modified Eagle Medium (DMEM) was used as the culture medium, however any basal medium suitable for use in the method might be used. Examples of basal media in addition to DMEM include RPMI, Basal Medium Eagle (BME), Ham's, Minimum Essential Medium Eagle (MEM), and Iscove's Modification of DMEM.

Culturing the isolated BM cells in low glucose is important for achieving priming or conditioning of the BM cells for further differentiation into endocrine hormone-producing cells. In the Examples section below, the low-glucose medium contained 5.5 mM glucose and 1% DMSO. Although these are suitable concentrations for use in the invention, other glucose and DMSO concentrations (e.g., about 4, 4.5, 5, 6, 6.5, or 7 mM glucose and about 0.1, 0.2, 0.3, 0.4, 0.5, 0.6, 0.7, 0.8, 0.9, 1.5, 2, 3, 4, 5, 6, 7, 8, 9, or 10% DMSO) would also likely suffice to prime the cells. The suitability of different glucose and DMSO concentrations for use in the first culturing step of the method of the invention can be empirically determined by testing different glucose levels under the conditions employed in the particular variation of the method of the invention that is to be used.

The second step in the method involves further culturing the BM cells in a high-glucose medium containing serum. This step induces differentiation of the BM cells into endocrine hormone-producing cells. The cells are typically cultured in the high-glucose medium for approximately 7 days (e.g., 4 to 9 days) before the cells begin to produce an endocrine hormone. As with the low glucose medium, the basal medium used in the high glucose medium can be DMEM or any other suitable medium. Any glucose concentration suitable for achieving differentiation of the BM cells into endocrine hormone-producing cells might be used. In the Examples section below, the high glucose medium contained 25 mM glucose. Although this is a suitable concentration for use in the particular method described, other high glucose concentrations (e.g., about 20–30 mM) would also likely induce endocrine hormone production. The suitability of different glucose concentrations for use in the second culturing step of the method of the invention can be empirically determined by testing different glucose levels under the conditions employed in the particular variation of the method of the invention that is to be used.

The inclusion of serum in the high glucose medium is important in inducing the cells to produce endocrine hormones. In the experiments described below in the Example section, 10% FBS was used. Other serum concentrations (e.g., 1 to 20%) and other types of serum (e.g., bovine calf serum, bovine neonate serum, adult bovine serum, as well as sera from other adult, neonatal, or fetal mammals) might also be suitable for use in the high glucose medium. The suitability of any particular percentage of serum and any particular type of serum can be determined by routine testing according to the methods taught herein.

Detection of Pancreatic Endocrine Hormones and
mRNAs

To determine whether BM cells are successfully differentiated into endocrine hormone-producing cells, the cells can be examined for expression of one or more pancreatic endocrine hormones, e.g., insulin (or precursors thereof such as pro-insulin and prepro-insulin), glucagon, pancreatic polypeptide, and somatostatin as well as hormone mRNAs. Hormone expression can be analyzed by any known technique. For example, antibody-based assays such as immunoprecipitation and Western blotting with anti-hormone (e.g., anti-insulin) antibodies can be used. To evaluate the functionality of in vitro-generated insulin-producing islet cells, radio-immunoassays (RIA) and enzyme-linked immunosorbent assays (ELISA) can be used to measure insulin release upon glucose stimulation.

To analyze hormone mRNA expression in a cell, a number of assays may be used, including Northern blotting and RT-PCR techniques. For example, to detect insulin, glucagon, somatostatin, and pancreatic polypeptide mRNAs in a sample using RT-PCR, total RNA is first isolated from pancreas and BM cells using any of a number of techniques known in the art. Once purified, the RNA is subjected to RT-PCR to generate cDNA. Resultant PCR products are then amplified using suitable primers and separated electrophoretically. Purified PCR products are then sequenced using any of a number of sequencing kits (e.g., AmpliTaq cycle sequencing kit, Perkin-Elmer Setus, Branchburg N.J.).

Regeneration of a Damaged Pancreas and Reversal of a Hormone Deficiency

The invention also includes methods for repairing a damaged pancreas in a subject. One such method includes the steps of providing a subject having a damaged pancreas (e.g., one having fewer islet cells than a non-damaged pancreas) and administering to the subject (e.g., a mammal such as a rodent or a human being having hyperglycemia caused by diabetes) at least one BM cell. The BM cells to be administered (e.g., transplanted) can be isolated from a mammal such as a rodent or human being. A related method of the invention utilizes transplantation of BM that have been differentiated into endocrine hormone-producing cells as described above, rather than simply isolated BM cells. In preferred variations of these methods, to avoid immune system-mediated rejection, the BM cells are isolated from the subject to be treated or from a histocompatible donor. The isolated BM cells or endocrine hormone-producing cells can be administered to the subject by any suitable technique. An example of a suitable cell transplantation protocol is described below. Techniques for the isolation of donor stem cells and transplantation of such isolated cells are also known in the art. See e.g., Sandhu et al., Am. J. Pathol. 159:1323–1334, 2001; Ianus et al., J. Clin. Invest. 111: 843–850, 2003; Yang et al., Proc. Natl. Acad. Sci. 99:8078–8083, 2002; Lumelsky et al., Science 292:1389–1394, 2001; and Soria et al., Diabetes 49:157–162, 2000.

To test the ability of donor-derived BM or hormone-producing cells to regenerate a damaged pancreas in a host animal, donor cells having a marker not present in the host animal can be transplanted into the host animal to create a chimeric animal. Based on expression of this heterologous marker, the presence of donor cells can be detected. Using such a method, the percentage of hormone-producing cells (e.g., beta-insulin producing cells) in the pancreas that are derived from the donor cells can be assessed. In the examples described below, donor and host rodents congenic for the cell marker DPPIV were used to test the ability of BM cells to regenerate a damaged pancreas. Any suitable marker, however, might be used.

Another method for testing the ability of donor-derived BM or hormone-producing cells to regenerate a damaged pancreas in a host animal can be performed by simply comparing regeneration of the organ (e.g., by gross or histological examination) in treated animals (i.e., those transplanted with BM or endocrine hormone-producing cells) to that in control animals (i.e., those not transplanted with BM or endocrine hormone-producing cells).

Treating a Pancreatic Disorder in a Subject

A particular application of the invention relates to treatment of an endocrine hormone deficiency incident to a pancreatic disorder. After transplanting BM or hormone-producing cells into a subject having a pancreatic disorder, hormone(s) secreted by the transplanted cells are released systemically to reduce or even reverse a hormone deficiency. For example, secretion of insulin by these cells could reduce or reverse hyperglycemia in a diabetic subject. The effectiveness of particular protocols can be assessed using conventional clinical assays, e.g., transplantation of donor cells into lethally irradiated animals and assessing regeneration of pancreatic cells, determining the animal's insulin secretion response to a high glucose challenge, its ability to normalize circulating glucose levels, and its ability to maintain glucose homeostasis.

Administration of Cells

The cells described above may be administered (transplanted) to animals including mammals (e.g., rats, humans) in any suitable formulation. For example, endocrine hormone-producing cells may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF.

The cells of the invention may be administered to animals by any conventional technique. The cells may be administered directly to a target site (e.g., a pancreas or liver) by, for example, injection or surgical delivery to an internal or external target site, or by catheter to a site accessible by a blood vessel. The cells may be administered in a single bolus, multiple injections, or by intravenous continuous infusion.

Effective Doses

The cells described above are preferably administered to a mammal in an effective amount, that is, an amount capable of producing a desirable result in a treated subject (e.g., regenerating pancreatic cells or reversing hyperglycemia and treating diabetes in the subject). As is well known in the medical and veterinary arts, dosage for any one animal depends on many factors, including the subject's size, body surface area, age, the particular mixture to be administered, time and route of administration, general health, etc. Depending on the size of the animal subject, between about 1–1000 IPC clusters can be administered, or between about 1 and $1 \times 10^8$ endocrine hormone-producing cells can be administered to the animal subject.

EXAMPLES

The present invention is further illustrated by the following specific examples. The examples are provided for illustration only and are not to be construed as limiting the scope or content of the invention in any way.

Example 1

Obtaining and Culturing BM Cells

BM cells were collected from the femurs and tibias of rats. The marrow cells were cultured in DMEM, low (5.5 mM)glucose (GIBCO cat.# 11885–084) supplemented with 10% FBS. After 60 minutes of incubation, non-adherent cells were collected and washed with serum-free DMEM medium. The cells were reinoculated in the serum-free DMEM medium at a cell density of $1\times10^5/cm^2$ in the presence of 1% DMSO for 3 days. The cells were then cultured in 10% FBS-containing medium in the high concentration glucose (25 mM, high glucose, DMEM, GIBCO, Catalogue # 11995–065) for 7 days. The cells were plated in plastic 6 well plates on slide coverslips (22×22 mm) coated with 0.3% type I collagen, which was extracted from the rat tail tendon by the method described by Michalopoulos and Pitot, Exp. Cell Res. 94:70–78 (1975).

Small spheroid clusters began to form at Day 7 under high-glucose conditions. After Day 10, the number and dimension of the spheroid cell clusters were considerably increased and formed a tightly organized mass of cells. Multiple clusters could be seen in single fields. At higher magnifications, the clusters appeared to have defined edges and structure. The 3-D cell growth morphologically resembled islet-like clusters, as described by Bonner-Weir et al., Proc. Natl. Acad. Sci. U.S.A. 97:7999–8004, 2000; Zulewski et. al., Diabetes. 50:521–533, 2001; Ramiya et al., Nat. Med. 6:278–282, 2000; and Yang et. al., Proc. Natl. Acad. Sci. U.S.A. 99:8078–8083, 2002. The level of glucose in the media had a significant effect on the number of clusters formed by the end of Day 10. High glucose culture conditions gave a mean cluster value of 157.5±32.9 clusters per coverslip (n=8 wells/3 separate experiments) while low glucose conditions produced 17.3±11.3 (n=8 wells/3 separate experiments) clusters per coverslip on a 22×22 mm coverslip. Additionally, the cluster size under low glucose conditions was markedly smaller as compared to that of high glucose conditions.

In another culturing method, BM cells were cultured in the presence of 1% DMSO for 3 days, and changed to DMEM containing 4.5 g/L glucose with 10% FBS for 7 days. To enable the detection of insulin secretion without interference from the fetal serum, the medium was then changed to serum-free medium. The serum-free medium was supplemented with 0.5% bovine serum albumin (BSA) and 5.5 mM glucose. The BM cells were incubated in the serum-free medium for 5 hours at 37° C. and washed twice with serum-free medium. The media was then changed to media containing high glucose (e.g., 25 mM) for 2 hours and the cells were incubated at 37° C. The culture-conditioned media were collected and frozen at −70° C.

Example 2

In Vivo Donor Cell Transplantation Assay

Donor DPPIV+ F-344 rats were purchased from Charles River Laboratories (Wilmington, Mass.). BM cells from house inbred normal male F-344 rats were transplanted into DPPIV-male F-344 rats subjected to a lethal dose of irradiation, approximately total doses were 800 rads (two doses of 400 rads) from a $^{137}$Cesium source. BM cells were obtained from femurs and tibias removed from the normal male F-344 rats sacrificed by Nembutal overdose (100 mg/kg) and disinfected by immersion in 70% ethanol. After the bones are removed and cleaned of skin and muscle, BM cells were exposed by cutting the ends of the bones and expelled by inserting a needle and forcing Iscove's medium supplemented with antibiotic solution through the bone shaft. BM cells were passed through a nylon mesh to remove any bone pieces that may contaminate the cell suspension. Approximately $60\times10^6$ male BM cells were transplanted via tail vein injection, and 30 days were allowed for the establishment of a chimeric system was evaluated by means of immunohistochemical analysis and PCR analyses of DPPIV from blood cells obtained from the tail vein bleeding. Only those animals expressing the DPPIV were placed on the pancreatic injury protocol (Fields et al., Pro. Soc. Exp. Bio. & Med. 186:183–187, 1987). After 6 weeks of a copper-deficient diet, animals were once again placed on a normal diet. Tissue was harvested at the indicated times during copper depletion and recovery periods. Subsequent to the administration of anesthesia, the entire pancreas was sampled from rats at 2, 4, 6, 8 and 10 weeks. Results from the immunohistochemical analysis of tissue samples are described below in Example 3.

Example 3

Immunohistochemistry of Cells

Immunohistochemical techniques were used to evaluate expression of DPPIV, pancreatic polypeptide, somatostatin, glucagon and insulin in cells sampled from pancreas tissue in transplant recipient animals. DPPIV activity was detected using the cytochemical method described by Lojdo et al. (Sb Lek. 81:200–7, 1979), which involves incubation of frozen sections with a DPPIV substrate, after fixation in acetone-ethanol (1:99, vol/vol) for 5 min at −20° C., and washing for 5 min in 95% ethanol at 4° C. The slides were air dried at room temperature. The substrate solutions were preparations of 2.5 mg gly-pro 4-methoxy-beta-naphtylamide (GPMN) in 150 ul of dimethylformamide, and 5 mg of Fast blue BB salt in 5 ml of TMS buffer (0.1 M Tris maleatol, 0.1M Nacl, Ph 6.5). The two solutions were mixed immediately before use and filtered. The slides were incubated in the substrate solution for 10–20 min at 37° C. The slides were washed twice with TMS buffer and incubated for 2 min in 0.1 M $CuSO_4$. The slides were rinsed again with TMS buffer and immediately counter stained with hematoxylin. In addition, frozen sections were fixed on 4% paraformaldehyde in PBS at room temperature for 15 min and then treated with 5% skim milk in PBS (a blocking medium) for 1 hr.

Immunofluorescent staining of pancreas tissue subsequent to transplantation and a copper-deficient diet using DPPIV-FITC and Insulin-Texas Red as markers was performed. Untreated DPPIV+ rat liver and pancreas were examined as controls. Insulin cells from an untreated DPPIV-deficient pancreas were not DPPIV+. There was no staining for DPPIV in either the untreated DPPIV-deficient pancreas or the untreated DPPIV-deficient liver. However, the beta cells did stain positive for insulin. Male rats were lethally irradiated and rescued with a BM transplant from a male animal. Engrafted male rats were then placed on the copper deficient diet protocol for a six-week period and placed back on a normal diet. Immunohistochemical localization of insulin and DPPIV in pancreas, after transplantation and copper deficient protocol (6-week time point) was analyzed. Two markers were used: DPPIV-FITC, Insulin-Texas Red. (A) Immunofluorescent staining of pancreas with insulin antibody, (B) Immunofluorescent staining of pancreas with DPPIV antibody. (C) Merge imaging of DPPIV expression in cells which co-expressed insulin. FIG. 1 shows expression of DPPIV cells in pancreas of BM transplanted animals. DPPIV expressing cell were counted at 2, 4, 6, 8, and 10 weeks in pancreatic tissues. In each of the BMTx DPPIV-deficient males, 60 sections were cut from frozen pancreas, stained and counted for the total number of DPPIV positive cells. White bar represents total DPPIV expressing cells and black bar represents DPPIV expressing cells in Langerhans Islet. Numbers are shown as percentages of Langerhans islet cells/total cells that were DPPIV positive.

Immunohistochemical techniques were also used to evaluate expression of insulin in BM cells cultured in vitro. Immunohistochemical localization of insulin in BM cells differentiated into pancreatic lineages in vitro was analyzed. Immunofluorescent staining with insulin and nuclear staining of a) control BM cells and b) BM cells cultured in 1% DMSO after 10 days was performed. Unlike the control BM cells, the cells cultured in 1% DMSO formed spheroid clusters and stained positive for insulin.

Example 4

RT-PCR and Northern Blot Analysis of Pancreatic Gene Expression

To determine whether the BM cell cultures differentiated to endocrine-hormone expressing cells, gene expression of endocrine cell hormones was measured using RT-PCR. To detect insulin, glucagon, somatostatin, and pancreatic polypeptide mRNAs, total RNA was isolated from the adult rat pancreas and BM cells were treated with 1% DMSO/DMEM low glucose (5.5 mM) medium (day 3), DMEM high glucose (25 mM) medium with 10% FBS (days 7 and 10), or non-cultured BM cells by the RNeasy kit (Quiagen, Valencia, Calif.). RT-PCR was performed as previously described (Oh et al., Biochem. Biophys. Res. Commun. 279:500–504, 2000). Two µg of RNA were used for cDNA synthesis. The resulting RT products were amplified under the following conditions: at 94° C. for 4 min followed by 30 cycle at 94° C. for 1 min, 60° C. for 1 min and 72° C. for 2 min, and then a final cycle at 72° C. for 4 min.

The insulin I primers delineated a 507-bp product. The insulin II primers delineated a 509-bp product. The glucagon primers delineated a 650-bp product or a 269-bp product. The somatostatin primers delineated a 456-bp product or a 301-bp product. The pancreatic polypeptide primers delineated a 587-bp product. The glyceraldehyde-3-phosphate dehydrogenase (GAPDH) primers delineated a 580-bp product. The amplified products were subjected to electrophoresis in 1.5% agarose gels and stained with ethidium bromide. The purified PCR products were directly sequenced using an AmpliTaq cycle sequencing kit (Perkin-Elmer Setus, Branchburg, N.J.).

The differentiated stem cells expressed insulin, glucagon, somatostatin, and pancreatic polypeptide. These results showed that primary adult BM stem cells can be differentiated in a non-lineage-restricted manner. Endocrine pancreatic mRNAs were not detected in the freshly isolated BM cells. RT-PCR revealed that expression of several of these genes did occur in BM cell cultures that had been treated with 1% DMSO. Insulin I and II, glucagon, somatostatin and pancreatic polypeptide mRNAs were detected during the initial 3 days of culture. Further investigation of cultures in high glucose DMEM with 10% FBS at Days 7 and 10 also showed the expression of these mRNAs. The PCR products were further analyzed by sequencing and compared to Gene-bank to confirm the data.

In another RT-PCR experiment, RT-PCR was carried out and RT-PCR was performed as previously described (Yang et al., Proc. Natl. Acad. Sci. U.S.A. 99:8078–8083, 2002). Oligonucleotide primers specific for rat pancreatic endocrine genes as described by Yang et. al., (Proc. Natl. Acad. Sci. U.S.A. 99:8078–8083, 2002) were used. The RT-PCR data demonstrated that the transcription factors, PDX-1, NKX2.2 and NKX6.1 are expressed early in the differentiation of the BM-derived cells and as the cells mature these transcription factors are down regulated. Mature endocrine genes such as those responsible for the production of glucagon, insulin, somatostatin, and pancreatic polypeptide were expressed later in their differentiation progress. The purified PCR products were directly sequenced for genetic confirmation. BM-derived cells stimulated by DMSO expressed some of the genes associated with mature pancreatic cells. These results suggest that BM-derived cells may include a pancreatic progenitor cell capable of progressing further toward a pancreatic fate.

In order to ascertain whether mRNA for insulin was present in the differentiated BM-derived cells, Northern blot analysis was performed using RNA from the high glucose cultured BM-derived cells, from INS-1 cells as a positive control (Hohmeier et al., Diabetes 49:424–30, 2000), normal liver as a negative control, and uncultured whole bone marrow cells for comparison. The high glucose cultured BM-derived cells showed insulin mRNA expression while the uncultured whole bone marrow cells did not.

Example 5

Measurement of Insulin Content and Secretion by Immunoprecipitation (Western Blotting and ELISA)

Detection of insulin, glucagon, somatostatin, and pancreatic polypeptide mRNAs was performed using the oligonucleotide primers for insulin, pancreatic polypeptide and GAPDH described in Example 4. BM cells were cultured in the presence of 1% DMSO for 3 days, and changed to DMEM with 4.5 g/L glucose with 10% FBS for 7 days. To enable the detection of insulin secretion without interference from the fetal serum, the medium Was then changed to serum-free medium. The serum-free medium was supplemented with 0.5% bovine serum albumin (BSA) and 5.5 mM glucose. The BM cells were incubated in the serum-free-medium for 5 hours at 37° C. and washed twice with serum-free medium. The media was then changed to media containing high glucose (25 mM) for 2 hours and the cells were incubated at 37° C. The culture-conditioned media were collected and frozen at −70° C. The insulin was then extracted with lysis buffer and detected by immunoprecipitation with a rabbit polyclonal anti-insulin antibody (Santa Cruz, Santa Cruz, Calif.) and Western blotting as described by Yang et al. (Proc. Natl. Acad. Sci. U.S.A. 99:8078–8083, 2002). Following immunoprecipitation, the precipitate material was analyzed by SDS-PAGE on 18% gels, transferred to nylon membranes, and blotted with anti-insulin antibody. Control samples consisted of normal rabbit serum and culture medium containing 0.5% BSA. Insulin was visualized by chemiluminescence.

The immunoprecipitation and Western blot analysis revealed that the differentiated BM-derived cells (BMD), or insulin producing cells (IPC) clusters, synthesized and stored detectable amounts of insulin during glucose challenge. During the glucose challenge, the cell lysate of the IPC clusters contained insulin in pro-form, while the media was shown to contain the active two-chain form of insulin.

To determine the amount of insulin secretion into the media, ELISA was performed on conditioned media using the 1-2-3 Ultra-Sensitive Rat Insulin ELISA kit (ALPCO Diagnostics). BMD IPC clusters (approximately 90 per experiment) were challenged with 25 mM glucose for 2 hours. Both H9-2 (83 clusters) and H8-2 (94 clusters) showed secretion of insulin into the media (177.8 ng/mL and 196.0 ng/mL, respectively). The IPC clusters exposed to low glucose conditions and media alone showed no reactivity to insulin in the assay. The results aid in demonstrating that BM-derived cells can be differentiated into endocrine-like cells producing active insulin when exposed to a glucose challenge.

Example 6

BMD Clusters and Ultrastructural Analysis of IPCs

Immunofluorescence analyses of BMD clusters were performed. Immunoactivity was detected using the cytochemical method by Oh et al. Biochem. Biophys. Res. Commun. 279:500–504. (2000). Sterile microscope cover slips were coated with rat tail collagen (RTC) and placed in a 6 well tissue culture plate. Differentiated BM-derived cells were grown until formation of spheroid colonies at approximately 10 days of culture. Clusters were hand picked and frozen in optimal cutting compound (OCT) at −70° C. and sections of 6 μm were placed on Superfrost Plus slides. Frozen sections were prepared by fixation in a 4% paraformaldehyde/PBS solution at room temperature for 15 minutes. The slides were then treated with a 5% skim milk in TBS-Ca (Tris-Cl, 50 mM $CaCl_2.H_2$), 1 mM, NaCl, 150 mM) blocking medium for 1 hour. Tissues were then reacted at 4° C. overnight with primary antibodies, such as mouse anti-rat DPPIV (BD Pharmingen, San Diego, Calif.), rabbit anti-rat insulin (Santa Cruz Biotechnology, Santa Cruz, Calif.), rabbit anti-rat pancreatic polypeptide (Dako Corp., Cambridge, Mass.), goat anti-rat somatostatin (Santa Cruz Biotechnology, Santa Cruz, Calif.), goat anti-rat glucagon (Santa Cruz Biotechnology, Santa Cruz, Calif.), or anti-rat C-peptide (Linco Research Inc., St. Charles, Mo.) which had been diluted at 1:100 with the blocking solution. After washing with PBS, tissues were incubated at 4° C. for 3 hr with the secondary antibody, Texas-red conjugated anti-goat/rabbit IgG antibody and FITC-conjugated anti-mouse IgG antibody (1:100 dilution with the blocking solution, Vecter Labs, Burlingame, Calif.), and with DAPI. (Vecter Labs, Burlingame, Calif.) for nuclear staining. The tissues were then observed under a fluorescent microscope.

The non-cultured BM-derived cells did not express insulin. However, the BM-derived cell clusters did express the cytoplasmic proteins of insulin, somatostatin and pancreatic polypeptide, which are all typically expressed in the cells of the islet of Langerhans. Approximately 80% of the total cell population of the BM-derived cell clusters corresponded to insulin-positive cells. The immunohistochemistry on BM-derived clusters revealed that the number of insulin-positive cells observed was considerably higher than the number of cells expressing either somatostatin or pancreatic polypeptide.

To assess for C-peptide expression and examine the mRNA expression for insulin via in situ hybridization (ISH), cryostat sections (6 μm thick) were fixed for 15 min in 4% paraformaldehyde. Following denaturation at 80° C. for 5 min, rat insulin digoxigenin labeled DNA probe (Roche, Basel, Switzerland) was applied to sections at 52° C. The sections were then coverslipped, sealed with rubber cement, and incubated in a hydrated slide box overnight at 52° C. The coverslips were removed in preheated 2×SSC buffer (pH 7.0) at 65° C. The sections were washed twice in preheated 50% formamide in 5×SSC buffer for 5 min (at room temperature) and washed twice in preheated 0.1×SSC buffer for 5 min each at 65° C. Color development was conducted at room temperature in Tris buffer (100 mM, 100 mM NaCl, 50 mM $MgCl_2$, pH 9.5) containing NBT and BCIP (Roche, Basel, Switzerland). Sections were mounted in Cytoseal (Richard-Allan Scientific, Kalamazoo, Mich.) after counterstaining with nuclear fast red (Vector Labs, Burlingame, Calif.).

Cells positive for C-peptide staining were seen throughout the clusters. High magnification photomicrographs showed a distinct pattern of positive staining similar to reported β-cell staining. When compared to INS-1 cells and pancreatic tissue, a similar staining pattern and level of expression was observed. In addition to the C-peptide staining, ISH on frozen sections of IPCs for insulin mRNA expression was conducted. The presence of insulin mRNA in the cytoplasm of the BM-derived cell clusters was observed using a digoxigenin-labeled insulin 1 oligonucleotide probe with colormetric detection, which gave a blue positive signal with nuclear fast red as a counter stain. The positive blue signal was seen peri-nuclear and radiated throughout the cytoplasm of the cells. The results indicate that BM-derived cells possess the potential to differentiate into cells found within the islets of Langerhans.

Example 7

Insulin Producing Cells (IPCs) Transplantation and Physiological Tests

The ability of BM-derived cell islet-like cell clusters to reverse hyperglycemia was examined in vivo using a STZ-induced diabetes NOD/scid mouse model. NOD/scid mice were chemically induced to a diabetic state through multiple treatments using a low dose of STZ. Following induction of the diabetic state, blood glucose levels were determined using a standard blood glucose meter every two days (One touch Profile, Diabetes tracking system, Johnson & Johnson Corn., Milpitas, Calif.).

Utilizing intraperitoneal injection of 40 mg/kg of streptozotocin (STZ) once a day for 5 days, diabetes was induced in 10-week-old male NOD/scid mice. For each injection, STZ is prepared by dissolution in 0.1 M citrate buffer (pH 4.5). Stable hyperglycemia (blood glucose levels 300–600 mg/dL as determined using a standard blood glucose meter) develops 5–6 days after the last STZ injections. Mice were then either engrafted (under general anesthesia) with 150 handpicked IPCs or they received a sham transplant of saline solution in the right subcapsular renal space. Roughly, 150 BMD IPC clusters Were transplanted to the renal subcapsular space of 9 diabetic mice.

Figure 2:
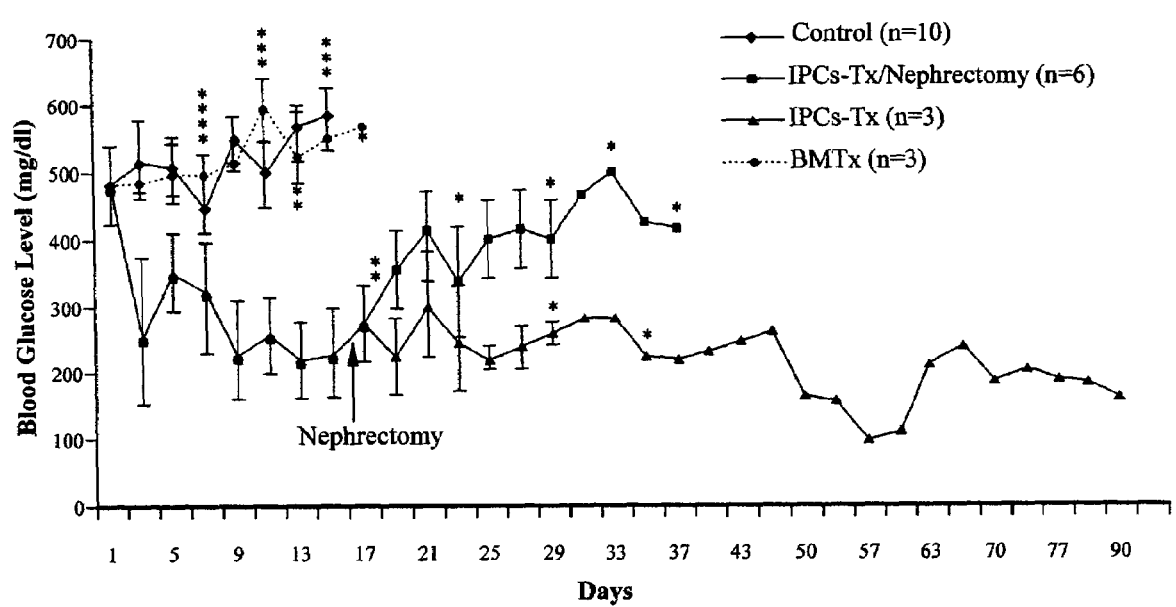
FIG. 2 is a graph displaying changes of IPC blood glucose levels over time after being transplanted into chemically induced diabetic mice. Shown in the graph are controls, STZ treated mice (no transplanted cells; n=10) or non-cultured BM cells (BM cells only; n=3), and mice transplanted with approximately 150 BM derived insulin producing clusters (n=9).

The mice receiving the transplant began to exhibit normalized blood glucose levels within 2–3 days. Approximately 17 days post-transplantation, 6 of the 9 mice underwent nephrectomy to remove the graft. As shown in FIG. 2, blood glucose levels were monitored every 2 days after transplantation and again following nephrectomy. The animals that did not receive a transplant or were transplanted with non-cultured BM cells remained hyperglycemic and did not survive more than 15 days post STZ treatment, indicating the protocol of STZ did destroy the β-cells of the pancreas causing the mice to die in a diabetic state. Animals that did receive a transplant were able to lower their glucose levels down to a fairly normal level within two days of transplant. To determine whether the transplanted clusters were responsible for the normalization of glucose levels, the IPC transplanted mice were separated into two groups. One group maintained the transplanted graft while the other group of transplanted mice underwent a nephrectomy to recover the grafted cells and test for euglycemia reversal. The kidneys in which the graft was placed were removed after 17 days and frozen in OCT for further examination. The mice that had the graft removed became hyperglycemic and died shortly thereafter. The animals that retained the transplanted IPC clusters were able to maintain fairly normal glucose levels for the remainder of the study and one animal survived out to 90 days post STZ treatment. This suggests that the clusters have the potential to undergo maturation to fully functioning-endocrine cells of the pancreas. Control animals that did not receive implants or received non-cultured BM cells exhibited persistent hyperglycemia followed by eventual death.

The removed kidneys, which received the transplanted cells, were further analyzed by conventional hematoxylin/eosin (H & E) staining, immunohistochemistry, and ISH for insulin and insulin mRNA as described in Examples 3 and 6. As seen by H & E staining, transplanted cells were viable and maintained their cluster formation, not incorporating themselves into the kidney. H & E staining revealed that the cells had become cuboidal in appearance, which is typical of the mature islet structure seen in adult pancreas. Insulin-positive cells were observed under the kidney capsule by immunohistochemistry and ISH. A digoxigenin labeled DNA probe was used to detect insulin mRNA expression. The grafted cells were positive for expression of the insulin mRNA. A negative control of non-transplanted kidney tissue was used for ISH and showed no positive signal throughout the section. The results support that BM-derived cell clusters retained their ability to secret insulin in vivo and functioned in response to the high blood glucose levels in the diabetic mice.

Example 8

Ultra-structural Analysis of IPC Clusters

IPC clusters were examined on an ultrastructural level. Electron microscopy was performed on day 10 IPCs to characterize the ultrastructure of these cells. IPC spheroids were fixed (0.1% glutaraldehyde/2% formaldehyde in 0.1 M cacodylate buffer), transferred to 0.1 M cacodylate buffer, and embedded. Ultra-thin sections were: treated with 10% $H_2O_2$, washed with 0.9% NaCl, blocked with 3% BSA, incubated overnight with the primary antibody in PBS supplemented with 0.5% BSA (rabbit anti-rat insulin, Santa Cruz), washed with PBS, and re-blocked with goat serum. Visualization of the binding of the primary antibody was achieved with gold labeled secondary antibody (15-nm gold particles, goat-anti-rabbit, Amersham Pharmacia), followed by counter-staining of the sections for electron microscopy.

The differentiated cell revealed structures typical of a secretory cell, containing rough endoplasmic reticulum, Golgi complex, a few large vacuoles and secretory vesicles containing dense granules. Secretory granules were densely packed within the cytoplasm of the differentiated cell. Along the cell membrane microvilli could be seen which has been reported to be another characteristic of mature β-cells. Many granules seen in BM derived IPC clusters were pale in nature with crystalline-like features. Immunogold electron microscopy showed that insulin was stored in the granules within the small secretory vesicles of the BM derived IPC clusters. Gold-labeling detected faint globular structures of differing size filled with floccular low density material and some granules with an electron dense core at the apical pole of the cells. Non-specific labeling was not observed in the nucleus or elsewhere throughout the cell. The fact that ultra-structural features that are typically found in the adult β-cell are also found in these IPC clusters indicates that these cells may have truly differentiated in culture into β-like cells capable of producing insulin.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of differentiating a mammalian bone marrow cell into an pancreatic hormone-producing cell, the method comprising the steps of:
    (A) providing the hone marrow cell;
    (B) first culturing the bone marrow cell in a low-glucose serum free medium comprising about 5.5 mM glucose and 1% DMSO for at least 3 days; and
    (C) then culturing the bone marrow cell in a high-glucose medium comprising about 25 mM glucose and 10% serum under appropriate conditions and for at least 7 days to promote differentiation of the cell into an pancreatic hormone-producing cell.

2. The method of claim 1, wherein the bone marrow cell is a rodent cell.

3. The method of claim 2, wherein the rodent cell is a rat cell.

4. The method of claim 1, wherein the pancreatic hormone-producing cell produces insulin.

5. The method of claim 1, wherein the pancreatic hormone-producing cell produces glucagon.

6. The method of claim 1, wherein the pancreatic hormone-producing cell produces somatostatin.

7. The method of claim 1, wherein the pancreatic hormone-producing cell produces pancreatic polypeptide.

8. The method of claim 1, wherein the high-glucose medium comprises DMEM and fetal bovine serum.

* * * * *

UNITED STATES PATENT AND TRADEMARK OFFICE
CERTIFICATE OF CORRECTION

PATENT NO. : 7,169,608 B2
APPLICATION NO. : 10/687674
DATED : January 30, 2007
INVENTOR(S) : Petersen et al.

Page 1 of 1

It is certified that error appears in the above-identified patent and that said Letters Patent is hereby corrected as shown below:

Col. 1, line 11, STATEMENT AS TO FEDERALLY SPONSORED RESEARCH, replace "This invention was made with United States government support under grant numbers DK60015 and DK58614 awarded by the National Institutes of Health. The United States Government may have certain rights in the invention." with --This invention was made with United States government support under grant numbers DK60015 and DK58614 awarded by the National Institutes of Health. The United States Government has certain rights in the invention.--

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,169,608 B2
APPLICATION NO. : 10/687674
DATED : January 30, 2007
INVENTOR(S) : Petersen et al.

It is certified that error appears in the above-identified patent and that said Letters Patent is hereby corrected as shown below:

Col. 1, STATEMENT AS TO FEDERALLY SPONSORED RESEARCH, replace "This invention was made with United States government support under grant numbers DK60015 and DK58614 awarded by the National Institutes of Health. The United States Government may have certain rights in the invention." with --This invention was made with United States government support under grant numbers DK60015 and DK58614 awarded by the National Institutes of Health. The United States Government has certain rights in the invention.--

Signed and Sealed this

Fourteenth Day of October, 2008

JON W. DUDAS
*Director of the United States Patent and Trademark Office*

UNITED STATES PATENT AND TRADEMARK OFFICE
CERTIFICATE OF CORRECTION

PATENT NO.       : 7,169,608 B2
APPLICATION NO.  : 10/687674
DATED            : January 30, 2007
INVENTOR(S)      : Bryon E. Petersen et al.

It is certified that error appears in the above-identified patent and that said Letters Patent is hereby corrected as shown below:

This certificate vacates the Certificate of Correction issued October 14, 2008. The certificate is a duplicate of the Certificate of Correction issued October 7, 2008. All requested changes were included in the Certificate of Correction issued October 7, 2008.

Signed and Sealed this

Twenty-fifth Day of November, 2008

JON W. DUDAS
*Director of the United States Patent and Trademark Office*